United States Patent [19]

Guo et al.

[11] Patent Number: 5,218,093
[45] Date of Patent: Jun. 8, 1993

[54] EGF VARIANTS AND PHARMACEUTICAL USE THEREOF

[75] Inventors: Zimin Guo, Weston; A. Michael Sills, Thornhill; Nigel A. Skipper, Toronto, all of Canada

[73] Assignee: Allelix Biopharmaceuticals, Inc., Ontario, Canada

[21] Appl. No.: 317,467

[22] Filed: Mar. 1, 1989

[51] Int. Cl.$^5$ .................. A61K 37/36; A61K 37/10; C12P 21/06
[52] U.S. Cl. .................. 530/399; 435/69.1; 435/70.1
[58] Field of Search .................. 514/12, 21; 530/399; 435/70, 69.1, 70.1

[56] References Cited

U.S. PATENT DOCUMENTS

| | | | |
|---|---|---|---|
| 4,764,593 | 8/1988 | Banks et al. | 435/70 |
| 4,783,524 | 11/1988 | Larsen et al. | 530/399 |

FOREIGN PATENT DOCUMENTS

| | | | |
|---|---|---|---|
| 1166983 | 5/1984 | Canada . | |
| 1213537 | 11/1986 | Canada | 195/1.14 |
| 2415101 | 4/1973 | Fed. Rep. of Germany . | |
| 2172890 | 10/1986 | United Kingdom . | |

*Primary Examiner*—Robert J. Hill, Jr.
*Assistant Examiner*—Shelly J. Guest
*Attorney, Agent, or Firm*—Foley & Lardner

[57] ABSTRACT

Biologically active variants of epidermal growth factor are provided, comprising tandemly linked units of monomeric EGF. The variants are useful per se as therapeutic agents to promote wound healing. Production of the multimeric EGF by genetically engineered microbial hosts is also described.

15 Claims, 4 Drawing Sheets

FIG. 1

```
SerArgAsnSerAspSerGluCysProLeuSerHisAspGlyTyrCysLeuHisAspGly
CTCTAGAAATAGTGACTCTGAATGTCCCCTGTCCCACGATGGGTACTGCCTCCATGATGG
------------------------------------------------------------60>
GAGATCTTTATCACTGAGACTTACAGGGGACAGGGTGCTACCCATGACGGAGGTACTACC
XbaI

ValCysMetTyrIleGluAlaLeuAspLysTyrAlaCysAsnCysValValGlyTyrIle
TGTGTGCATGTATATTGAAGCATTGGACAAGTATGCATGCAACTGTGTTGTTGGCTACAT
------------------------------------------------------------120>
ACACACGTACATATAACTTCGTAACCTGTTCATACGTACGTTGACACAACAACCGATGTA
                       SphI

GlyGluArgCysGlnTyrArgAspLeuLysTrpTrpGluLeuArgEND
CGGGGAGCGATGTCAGTACCGAGACCTGAAGTGGTGGGAACTGCGCTGAATTCC
-----------------------------------------------------174
GCCCCTCGCTACAGTCATGGCTCTGGACTTCACCACCCTTGACGCGACTTAAGG
                                              EcoRI
```

Construction of plasmid pZM-220.
(▭ ALCA1 promoter, ▨ synthetic signal,
▭ hEGF,
▨ 3' flanking region of glucoamylase.)

Construction of plasmid pME1 (EGF dimer).

( ▒▒▒ ALCA1 promoter, ▨▨▨ synthetic signal,
☐ hEGF,
▓▓▓ 3' flanking region of glucoamylase.)

Linker of the tandem EGF dimer.

Construction of plasmid pME2 (EGF trimer).
( ▫▫▫▫ ALCA1 promoter, ▨▨▨▨ synthetic signal,
▭ hEGF,
▦▦▦▦ 3' flanking region of glucoamylase.)

Linker of the tandem EGF trimer.

EGF VARIANTS AND PHARMACEUTICAL USE THEREOF

FIELD OF THE INVENTION

This invention relates to biologically active variants of epidermal growth factor, to methods for their manufacture and to their use in wound healing applications.

BACKGROUND TO THE INVENTION

Epidermal growth factor, hereinafter referred to as EGF, is a biologically potent, monomeric protein produced naturally by many species of mammals including humans. It stimulates the growth of new skin and other epithelial tissues and thus has great potential as a therapeutic agent in corneal transplant healing, in skin regeneration e.g. for treating burns and grafts, and in wound healing e.g. for treating surgical incisions and stomach and other ulcers.

A genetic engineering approach has been adopted to produce EGF in amounts sufficient to meet commercial demands, although difficulties have been encountered. Like many other proteins produced nakedly in recombinant microbial hosts, EGF is degraded intracellularly by the action of native proteases and only modest yields are attainable. To protect EGF from protease action and elevate yields, EGF is now typically produced as a fusion protein, bound to a stabilizing carrier protein that inhibits EGF degradation (see, for example, EP 234,888). For use in therapeutic applications, the EGF is liberated from the carrier protein and then purified. In economic terms, the advantage of increased yields offered by the fusion protein technology must be weighed against the disadvantage of the laborious downstream processing required to release and recover EGF in its authentic, monomeric form.

An alternative strategy for producing protease-sensitive proteins in microbial hosts has been proposed in the literature. According to this proposal, the host is transformed to express the desired protein in a multimeric form that comprises repeating units of the desired protein linked tandemly through a cleavage-sensitive site. Following recovery of the protein multimer, the desired monomeric form of the protein is liberated for pharmaceutical use by digestion with the appropriate cleavage agent, usually a site-specific enzyme. The general concept is described in Canadian patent 1,213,537. It has been suggested that EGF may be produced using this strategy (see GB 2,172,890).

The strategy of producing EGF either as a fusion protein or as a multimer is attractive in the sense that the EGF is rendered more stable in the microbial host. However, because its biological activity can be eliminated or significantly impaired when it is bound to other protein moieties, time consuming efforts are employed to recover and purify EGF per se from the hybrid protein. Moreover, it is often necessary to modify the structure of EGF so that the selected cleavage site remains unique, and the EGF molecule is not cleaved internally by the technique designed to liberate it.

It is an object of the present invention to provide a method for producing proteins having the biological activity of EGF.

It is another object of the present invention to provide biologically active variants of EGF.

It is a further object of the present invention to provide pharmaceutical compositions useful to promote wound healing.

It is another object of the present invention to provide a method for treating wounds to promote healing thereof.

SUMMARY OF THE INVENTION

It has now been determined that multimeric forms of EGF, in which two or more EGF units are linked tandemly, possess biological activity characteristic of EGF in its monomeric form. Thus, in sharp contrast to prior art proposals suggesting that multimeric forms of EGF are to be cleaved to release individual units of monomeric EGF, the present invention contemplates the use of multimeric EGF per se in formulating pharmaceutical compositions and to treat wounds to promote healing thereof.

In accordance with one aspect of the present invention, there is provided a pharmaceutical composition for use in treating wounds to promote healing thereof which comprises multimeric EGF and a pharmaceutically acceptable carrier therefor, said multimeric EGF comprising at least two tandemly linked EGF units.

In accordance with another aspect of the present invention there is provided a method for treating wounds to promote healing thereof which comprises administering a pharmaceutical composition comprising multimeric EGF.

In another aspect of the invention there are provided novel multimeric forms of EGF comprising at least two EGF units linked tandemly either by direct C-terminus to N-terminus fusion or through a cleavage-insensitive peptide linker.

According to another aspect of the invention, there is provided a method for producing novel EGF multimers which comprises culturing a microbial host that has been genetically engineered to produce a novel EGF multimer as defined hereinabove, and recovering the resultant multimer.

DETAILED DESCRIPTION OF THE INVENTION AND PREFERRED EMBODIMENTS

One aspect of the invention relates to multimeric forms of EGF that exhibit EGF biological activity and comprise at least two tandemly linked EGF units. In the context of the present specification, the term "EGF unit" is intended to encompass authentic full length forms of monomeric EGF, and fragments and analogues thereof having biological activity similar to that exhibited by authentic EGF as measured in recognized bioassays such as the epidermal growth factor receptor binding assay described by Savage et al in *Analytical Biochem.*, 1981, 111, pp. 195 et seq. An EGF unit may have an amino acid sequence based on EGF of human, murine or other origin.

Multimers of human EGF may, for example, comprise EGF units corresponding to the authentic form of human EGF having 53 amino acid residues arranged in the sequence reported by Gregory et al in *Nature*, 1975, 257, 325–327; biologically active fragments thereof such as fragments lacking one or more C-terminal and/or N-terminal residues of the authentic form, i.e. EGF1-52, EGF1-51, EGF1-50, EGF1-49 and EGF1-48; and biologically active analogues of the authentic or fragment forms including analogues bearing one or more amino acid substitutions or additions e.g. [Asp$^{25}$]EGF, [Pro$^{52}$-

]EGF, [Arg$^{53}$]EGF, [Val$^{21}$]EGF, [Pro$^{52}$Pro$^{53}$]EGF and [Met$^{-1}$]EGF. Similarly, authentic or variant forms of murine EGF may be employed as EGF units when murine EGF multimers are desired. Such murine EGF units may be selected from the authentic form of murine EGF having 53 amino acids arranged in the sequence reported by Savage et al in *J. Biol. Chem.*, 1972, 247, 7612–7621; or fragments thereof such as those described in U.S. Pat. Nos. 3,917,824; 3,948,875; 4,032,633; and 4,035,485; or biologically active analogues of authentic murine EGF.

EGF multimers of the invention comprise at least two EGF units that are linked tandemly i.e. C-terminus to N-terminus. Units may be linked either through an amide bond or through a peptide linker. If a peptide linker is to be incorporated between the EGF units, its length and amino acid structure should be selected so as not to detract significantly from the biological activity of the resulting multimer. It is highly preferable to avoid incorporating cysteine residues in the linker, for example, so that cystine bridges may form properly within the EGF units of the multimer. Also, the sequence of amino acids in the linker are preferably selected so that cleavage by enzymes native to the microbial production host is avoided. Linkers not exceeding about 50 amino acid residues may be used. Further, since the multimers of the present invention are per se biologically active, and need not serve as sources of monomeric EGF, linkers that are insensitive to post-production cleavage agents may be incorporated. In general, linkers not exceeding about 50 amino acid residues, preferably not more than about 10 residues, may be employed.

The EGF multimers of the invention comprise at least two, preferably two or three, and usually not more than about seven EGF units linked in the manner just described. It should be appreciated that an EGF multimer may be chimeric in the sense that murine EGF units and human EGF units may be linked in the multimer. Preferably, all EGF units within the multimer are of the same type e.g. all human EGF units, so that adverse immune reactions are limited during treatments using the multimer. It will be further appreciated that a human EGF multimer may comprise human EGF units of different amino acid sequence. For example, a multimer may comprise one human EGF unit having an amino acid sequence corresponding to authentic human EGF, linked with a unit of human EGF analogue, in turn linked to a unit of human EGF fragment etc.

The production of EGF multimers of the various types described above can be achieved by applying the art of recombinant DNA technology to any of a variety of microbial hosts for which such techniques have already been developed, including bacterial hosts such as E. coli, Streptomyces and Bacillus; fungal hosts such as Saccharomyces, Pichia and Aspergillus; and insect cell hosts and mammalian cell hosts such as CHO cells and COS cells. In general, the technique involves transformation of the selected host with a DNA construct in which DNA coding for the desired EGF multimer is linked operably with DNA enabling its expression in the selected host. Transformed host cells are then cultured selectively in a suitable culturing medium under conditions permitting production of the multimer and the multimer is then recovered using available biochemical extraction techniques.

DNA coding for the desired EGF multimer may be obtained directly by DNA synthesis. The block ligation approach may be employed whereby 10- to 15-mer oligonucleotide pairs are ligated in correct succession by overhand complementarity. DNA coding for monomeric EGF has been successfully produced using this technique (for guidance see EP 046,039 and EP 131,868). Because of the relative greater length of multimeric EGF-encoding DNA, synthesis thereof is more preferably accomplished using the enzymatic fill-in technique described originally by Rossi et al (*J. Biol. Chem.*, 257, 16, pp. 9226–9229, 1982). In this technique, long (30- to 100-mer) single-stranded oligonucleotides are designed to be annealed in a short region of complementarity and then "filled-in" using polymerase and a pool of nucleotides, to provide the desired double-stranded DNA molecule.

DNA coding for multimeric EGF may also be obtained by assembling DNA fragments coding for monomeric EGF, using now standard cloning techniques. DNA coding for the monomer may be isolated from an appropriate cDNA library or may be synthesized as just described and then cloned in tandem on an appropriate cloning vehicle such as a plasmid or phage. Specific alterations to the resultant multimer-encoding DNA may then be effected using the oligonucleotide-directed site-specific mutagenesis approach described by Kunkel et al (*Proc. Natl. Acad. Sci. USA*, 1985, Vol 82, pp. 488–492). This technique enables the addition, deletion or substitution of DNA into the DNA construct and will therefore be useful for converting one form of multimer-encoding DNA to another, alternative and perhaps more desirable form. It will be appreciated then that it is possible to prepare various forms of multimer-encoding DNA using this technique from a prototype construct prepared either entirely by synthesis or by tandem assembly of isolated EGF-encoding DNA.

To engineer a selected microbial host genetically to produce the desired EGF multimer, a cloning vehicle comprising the multimer-encoding DNA linked operably with DNA enabling expression thereof in the selected host is first obtained and then incorporated into the host using established transformation protocols. The cloning vehicle is preferably a plasmid harbouring DNA serving such other functions as are required by the selected host recipient. When bacterial cells such as E. coli and yeast cells such as *Saccharomyces cerevisiae* are to serve as host, the plasmid preferably also encodes a replication function enabling the plasmid to be maintained autonomously in the host. In addition, the plasmid also preferably codes for a product enabling plasmid-harbouring hosts to be cultured selectively.

In a particularly preferred embodiment of the invention, the selected host is engineered to secrete the EGF multimer. Secretion of the multimer will facilitate formation of the cystine bridges necessary for the proper biological functioning of the individual EGF units comprised by the EGF multimer. To provide for secretion of the multimer, cloning vehicles are employed in which DNA coding for a signal peptide is linked operably to the EGF multimer-encoding DNA. Such cloning vehicles are available for use in the vast majority of microbial hosts in current use for recombinant protein production.

Transformed microbial hosts produced as described above are then cultured in a growth supporting medium under conditions permitting production of the EGF multimer. Conditions most appropriate for culturing will be dictated by the nature of the host and by any additional requirements of DNA elements controlling multimer DNA expression.

Strategies for recovering the multimer produced by the microbial host may involve lysing harvested cells to recover a protein pellet from which the multimer may be extracted and purified using standard biochemical techniques. More preferably, the multimer is recovered from the medium in which hosts engineered to secrete the multimer have been cultured.

The EGF multimer may be purified using biochemical techniques standard in the art, such as those techniques which separate proteins according to size, hydrophobicity, charge and affinity. The size of the multimer, its charge and its hydrophobicity are all generally predictable by analogy with natural EGF i.e. EGF dimers lacking large peptide linkers are generally twice the size of and exhibit twice the hydrophobicity and charge of natural EGF, whereas EGF trimers exhibit three-fold enhancement of these properties, etc. Accordingly, reports describing the purification of natural EGF can be useful in developing protocols for purifying the multimers, although, clearly, the particular protocol must take into account the nature of the contaminants present in the sample from which the multimer is to be recovered. Multimeric forms of EGF retain the ability to bind antibody specific for natural EGF. Accordingly, affinity columns bearing covalently-linked anti-EGF antibody may be used in the typical manner to purify the multimeric EGF.

After purification, the multimer may be lyophilized for later use or formulated directly into pharmaceutical compositions suitable for treating wounds to promote healing thereof. Such compositions may be of a type already established for administering monomeric EGF such as gels, solutions, suspensions or dispersions optionally stabilized with a water soluble cellulose derivative in the manner detailed in U.S. Pat. No. 4,717,717. Creams, lotions and ointments comprising multimeric EGF may be applied topically to promote wound healing. Cream formulations of multimeric EGF suitably comprise surface active agents such as derivatized fatty acids or sorbitol, an oil based carrier composed of petroleum jelly, paraffin or the like, water, and such other excipients as are used routinely in the art to formulate proteinaceous active ingredients. Reference may be made to EP 205,051 for guidance in formulating EGF creams.

When combined with an opthalmologically compatible carrier, multimeric EGF will be useful to promote healing of corneal damage. Solutions of EGF may, for example, be applied as eye drops. Corneal mortar compositions may also be employed, as detailed in EP 240,031.

To inhibit gastric acid secretion i.e. for use in treating stomach ulcers, the multimeric EGF is preferably ingested in the form of tablets or capsules. Alternatively, buffered solutions thereof may be administered by injection.

The unit dose of multimeric EGF required for treatment will of course depend on the mode of administration and the severity of the wound to be treated. In general, dosage sizes may be patterned on those suitable in the administration of monomeric EGF, having regard for any variations in specific activities between these forms of EGF.

BRIEF DESCRIPTION OF THE DRAWINGS

Specific embodiments of the invention are hereinafter described with reference to the accompanying drawings in which:

FIG. 1 provides the nucleotide and corresponding amino acid sequence of a synthetic Xba1/EcoRI cassette coding for authentic human EGF;

Using the enzymatic fill-in strategy described originally by Rossi et al (*J. Biol. Chem.*, 1982, 257, 16, pp. 9226-9229) human EGF-encoding DNA having the sequence reported by Bell et al (*Nucleic Acids Research*, 1986, 14, pp. 8427-8466) was synthesized as an Xba1-/EcoR1 cassette bearing a 3' TGA stop codon and an internal Sph1 site. In particular, the Xba1/EcoR1 cassette was prepared from two oligonucleotides synthesized individually on an Applied Biosystems model 380B synthesizer i.e. a 100mer equivalent to the 5' half of the coding strand and a 90-mer equivalent to the 5' half of the non-coding, complementary strand. The two oligos were designed to incorporate a 16-mer region of complementarity at their 3' ends to permit annealing thereof. After annealing, the two 3' ends were extended enzymatically using Sequenase ™ (a product of U.S. Biochemicals) in the presence of dNTP's to "fill-in" the remaining gene sequence. The resulting double-stranded cassette was then restricted with Xba1 and EcoR1 and cloned into a phagemid vector, in this case a pTZ derivative, for sequencing and amplification. FIG. 1 provides the nucleotide sequence of the resulting cassette (hereinafter the "EGF cassette"). Solid lines are used to identify the oligos used in its construction.

Figure 2:
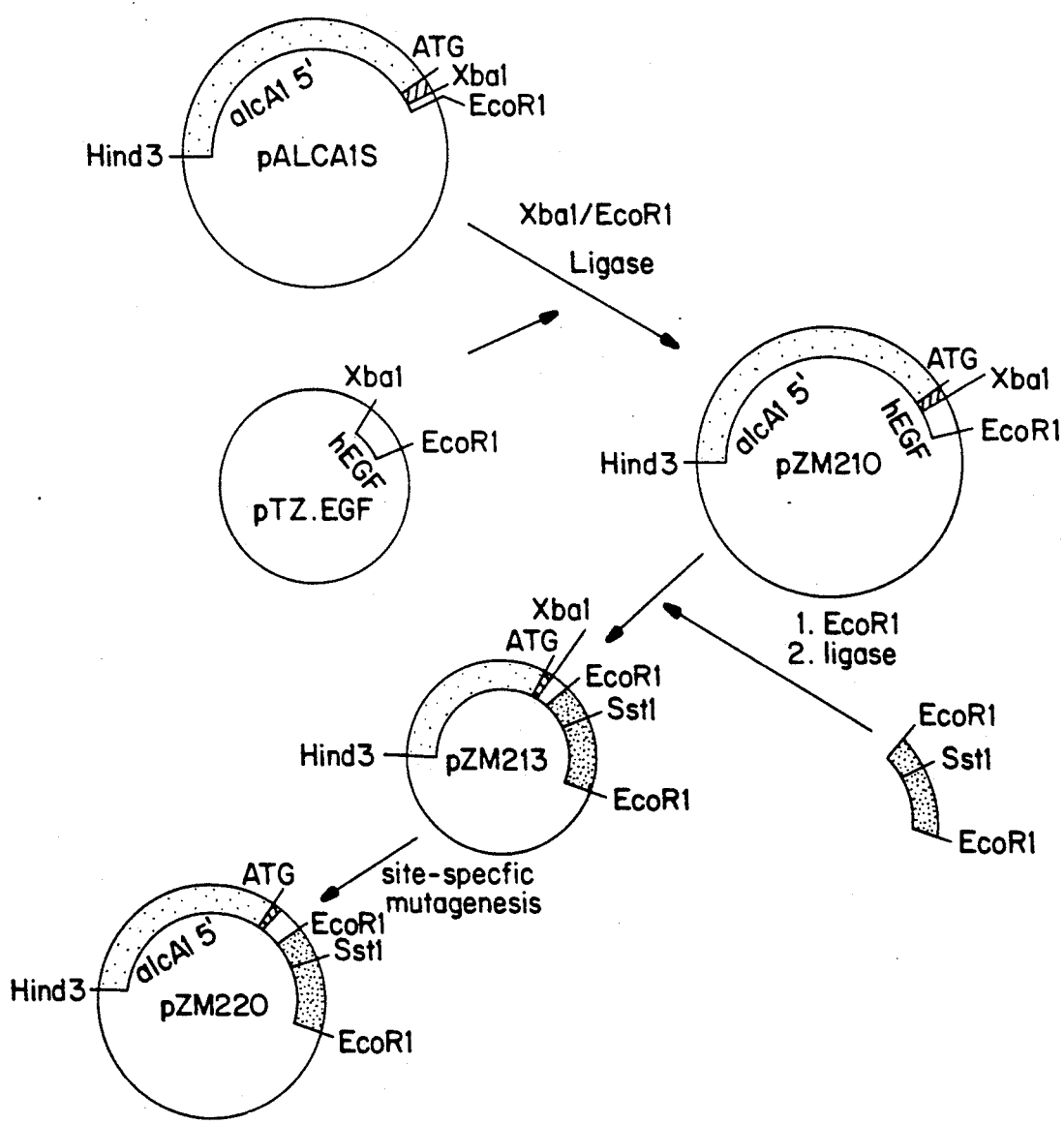
FIG. 2 depicts schematically the construction of pZM-220, an Aspergillus secretion vector harbouring EGF monomer-encoding DNA.

For the ultimate goal of providing a microbial host capable of secreting multimeric EGF, the EGF cassette coding for monomeric EGF was liberated from the phagemid vector and then cloned as such into the Xba1-/EcoR1 sites of Aspergillus nidulans secretion vector pAlcA1S to generate pAlcA1S-EGF. Plasmid AlcA1S, described in more detail by Gwynne et al in *Bio/Technology*, 1987, 5, 713-719 incorporated herein by reference, is a pUC12 derivative having a multiple cloning site (including a 5'-Xba1/EcoR1-3' region) immediately downstream of synthetic DNA coding for a consensus signal peptide (17-mer), expression of which is controlled by the promoter region of the alcohol dehydrogenase 1 gene of A. nidulans. To provide a transcriptional terminator and polyadenylation site downstream of the EGF-encoding DNA, a 1 kb fragment of the 3' untranslated region of the A. awamori glucoamylase gene (see Nunberg et al, *Mol. Cell. Biol.*, November 1984, 2306-2315) was cloned into the EcoR1 site of pAlcA1S-EGF, thereby generating a plasmid designated pZM-213. Superfluous codons (a cloning artefact) between the signal sequence and the EGF gene were then removed using the oligonucleotide-directed in vitro mutagenesis technique. In the resulting plasmid, designated pZM-220, synthetic DNA coding for monomeric human EGF is fused directly with the signal sequence to enable secretion thereof in an Aspergillus host, and is linked 5' to the AlcA1 promoter region and 3' to a transcriptional terminator. The ZM-220 plasmid served as a template to generate plasmids coding for multimeric human EGF. Construction of pZM-220 is depicted schematically in FIG. 2.

Construction of plasmid encoding multimeric EGF

Figure 3:
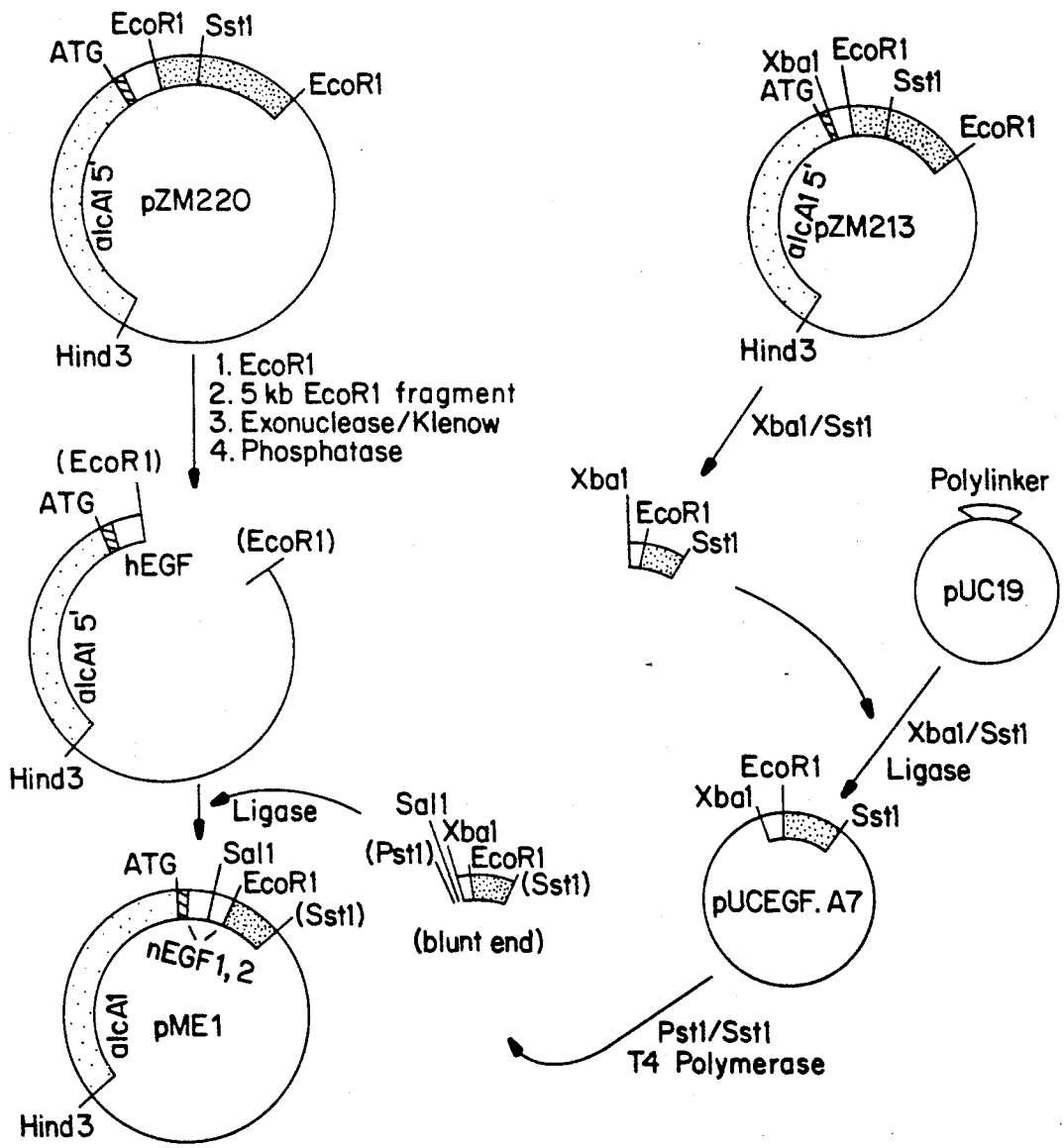
FIG. 3 depicts schematically the construction of pME1, an Aspergillus secretion vector harbouring DNA coding for EGF dimer.

To generate a plasmid coding for dimeric EGF, a DNA fragment coding for monomeric EGF was linked tandemly downstream of the EGF-encoding insert on pZM-220. In particular and with reference to FIG. 3, pZM-220 was digested with EcoRI and then treated with nuclease to eliminate the stop codon at the 3' end of the EGF insert. For ligation downstream thereof, EGF monomer-encoding DNA was liberated from pZM-213 as an Xba1/Sst1 fragment which includes the translational stop codon and the major and necessary portion of the glucoamylase transcriptional terminator. After cloning into pUC19, to form intermediate plasmid pUCEGF.A7, the fragment was liberated by Pst1/Sst1 digestion, blunt-ended and then cloned by blunt end ligation into pZM-220 linearized as described above.

Figure 3A:
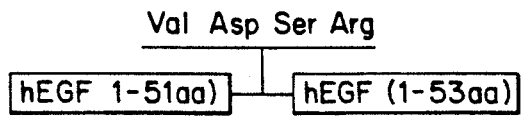
FIG. 3a depicts the arrangement of EGF units in the EGF dimer encoded on pME1.

As a consequence of the cloning steps used in its construction, the resulting plasmid pME1 comprises an EGF dimerencoding insert in which an upstream EGF1-51 unit is linked tandemly, without stop codon interruption, to a downstream unit of EGF1-53 by a tetrametic peptide linker. Also retained operably on pME1 are the alcA1 promoter, consensus signal sequence fused directly with the EGF dimer-encoding insert and the transcriptional terminator, to enable the EGF dimer to be expressed and secreted from an Aspergillus host. Arrangement of EGF units in the EGF dimer encoded on pME1 is represented in FIG. 3a.

Figures 4, 4A:
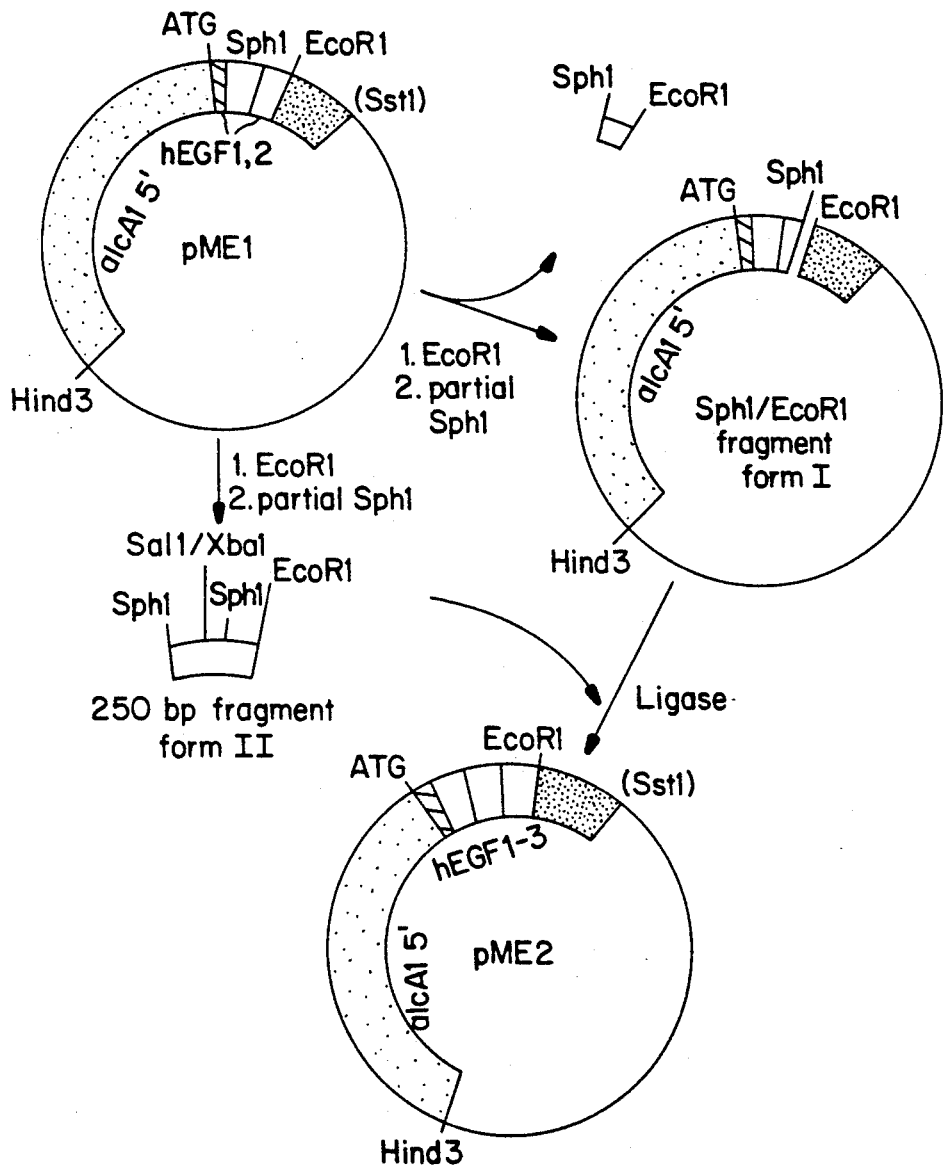
FIG. 4 depicts schematically the construction of pME2, an Aspergillus secretion vector harbouring DNA coding for EGF trimer.
FIG. 4a depicts the arrangement of EGF units in the EGF trimer encoded on pME2.

To provide a plasmid coding for trimeric EGF, a third human EGF unit was introduced onto pME1 in the manner depicted in FIG. 4. First, a 3' portion of the downstream unit was removed from pME1 by EcoRI and partial Sph1 digestion. This 3' portion was replaced by a larger Sph1/EcoRI fragment obtained from a second sample of pME1 which not only restored the deleted portion of the downstream EGF unit, but also incorporated a third EGF unit together with the stop codon and transcriptional terminator. The resulting plasmid, designated pME2, thus comprises DNA coding for an EGF multimer, in this case an EGF trimer, in which an EGF1-51 unit is linked tandemly through a peptide tetramer to a second EGF1-51 unit, which in turn is linked downstream to an EGF1-53 unit by another peptide tetramer. The arrangement of EGF units in the EGF trimer encoded on pME2 is represented in FIG. 4a.

It will be appreciated that the strategy just described for constructing the trimer-encoding construct is also useful for preparing constructs coding for four or more tandemly linked EGF units.

Expression of multimeric EGF

In separate experiments, Aspergillus nidulans strain T580 (a pyrG⁻ mutant) was co-transformed with plasmid FB94 which comprises the wild type pyrG gene of A. nidulans in pUC12, and either pME1 or pME2, according to the general method reported by Yelton et al, *Proc. Natl. Acad. Sci. U.S.A.*, 81, 1370–1374. Transformants were grown initially on fungal complete medium plates at 37° C. for three to four days. The spores were then removed from the plates and cultured in 500 ml minimal medium supplemented with 100 mM threonine and 0.1% fructose ($2 \times 10^6$ spores/ml in 2.8L flasks) and then incubated at 37° C. with shaking.

After culturing for 48 hours, spent culture medium was recovered, microcloth-filtered and then analysed for EGF activity.

Assays for EGF activity

Individual samples of medium recovered as described above from cultures of the A. nidulans hosts were assayed initially for EGF activity by competitive radioimmunoassay, using the EGF RIA kit available from Amersham International plc (product code IM.1961) in the manner specified by that supplier. Initial results indicated that about 50% of the putative Aspergillus transformants had secreted a substance capable of both binding to the anti-EGF antibody and competing with $^{125}$I-labelled EGF for binding to the antibody. It was further noted that media obtained from EGF multimer-producing pME1 and pME2 transformants exhibited from four to five times the activity detectable in media recovered from the EGF monomer-producing pZM-220 transformants. This suggested that higher levels of EGF product can be recovered from the multimer-producing transformants than from the monomer-producing transformants grown under substantially identical conditions, and tends to confirm that EGF is far more stable in multimeric form than in monomeric form.

Supernatants obtained from the RIA-positive transformants were than analyzed by SDS-PAGE after having been concentrated and partially purified by desalting on a C18 reverse-phase cartridge. When supernatants recovered from pZM-220 transformants were run, a protein band exhibiting the 5.5 kD size characteristic of monomeric EGF was identified, as expected. A predominant band of about twice the molecular weight of monomeric EGF was observed when supernatants of the EGF-dimer producing pME1 transformants were run. Similarly, a predominant band of about 16.5 kD, i.e. about three times the size of monomeric EGF, was observed when supernatants of the EGF trimer-producing pME2 transformants were run.

The subject protein bands were subsequently analyzed by Western blot and found to have immunoreactivity with anti-human EGF antibody.

Having thus confirmed that transformants were producing protein having the immunological characteristics of EGF and a molecular size consistent with the expected size of dimeric EGF and trimeric EGF, the EGF multimers were examined for biological activity in a competitive receptor binding assay. More particularly, dimeric and trimeric EGF were evaluated for their ability to compete with a labelled EGF standard for binding to EGF receptors available on membrane preparations of the cell line A431. Briefly, the receptor binding assay was conducted in the manner reported by Savage et al in *Analytical Biochem.*, 1981, 111, pp. 195 et seq. using the $^{125}$I-labelled f-Met analogue of human EGF available from Amersham International plc as competing agent. It was found that both dimeric EGF and trimeric EGF are able to bind to EGF receptor and compete with labelled monomeric EGF for receptor sites, thereby confirming that multimeric forms of EGF retain the biological activity characteristic of monomeric EGF. Surprisingly, biological epidermal growth factor activity is not destroyed or significantly impaired by the linking of one EGF unit with another.

The dimeric product produced by the pME1 transformants was subsequently purified for analysis. To purify the EGF dimer, 3–4 liters of medium in which pME1 transformants had been cultured were acidified to pH 3.9 with glacial acetic acid and then loaded onto a 1.2 liter preparative S-Sepharose fast flow column (Pharmacia, Inc.). The column was washed with 40 mM ammonium acetate at pH 3.9 at a flow rate of 5 ml/min. The active fraction was eluted using 1M ammonium acetate at pH 4.1 and then lyophilized.

Salts were then removed from the concentrated sample using a column of C18 Corasil media (Waters Inc.) with a bed volume of 50 ml. Samples were loaded into the column at a flow rate of 2 ml/min, washed with water and eluted with 40% acetonitrile. The active peak was then freeze-dried.

In the final purification step, the dried sample was resuspended into 3 ml starting buffer (20 mM Tris-HCl, pH 8.0) and loaded onto a Mono Q HR 10/10 anion exchange column (Pharmacia Inc.) equilibrated with the starting buffer. After extensive washing with buffer, dimeric EGF was eluted using a linear gradient from 0 to 0.5M NaCl at pH 8.0.

When analyzed by SDS-PAGE, the purified product migrated as a single, silver-stained band of about 11 kD. Western blotting of pure samples with rabbit anti-EGF antibody confirmed the purity of the sample.

We claim:

1. A pharmaceutical composition comprising EGF multimer and a pharmaceutically acceptable carrier therefor, said multimer comprising at least two tandemly linked EGF units.

2. A composition as defined in claim 1 wherein said multimer comprises tandemly linked human EGF units.

3. A composition as defined in claim 2 wherein said multimer consists of two tandemly linked human EGF units.

4. A composition as defined in claim 2 wherein said multimer consists of three tandemly linked human EGF units.

5. A method for treating a wound to promote healing thereof which comprises administering a pharmaceutical composition as defined in claim 1.

6. The method according to claim 5 wherein said composition is administered by topical application to said wound.

7. An EGF multimer comprising at least two EGF units linked tandemly by direct C-terminus to N-terminus fusion or through a cleavage-insensitive peptide linker.

8. An EGF multimer as defined in claim 7 wherein said EGF units are human EGF units.

9. An EGF multimer as defined in claim 8 which consists of two tandemly linked human EGF units.

10. An EGF multimer as defined in claim 8 which consists of three tandemly linked human EGF units.

11. A method for producing a protein having EGF activity which comprises culturing a microbial host transformed by a DNA construct in which DNA coding for an EGF multimer as defined in claim 7 is linked operably with DNA enabling expression thereof in said microbial host, and recovering the EGF multimer so produced.

12. The method according to claim 11 wherein said DNA construct further comprises DNA coding for a signal peptide to enable the multimer to be secreted from the microbial host.

13. The method according to claim 12 wherein said microbial host is an Aspergillus host.

14. The method according to claim 13 wherein the EGF multimer is recovered from the medium in which the Aspergillus host is cultured.

15. An EGF multimer as defined in claim 7, comprising at least two EGF units linked tandemly by direct C-terminus to N-terminus fusion.

* * * * *